United States Patent [19]

Pedersen

[11] 3,954,959

[45] May 4, 1976

[54] ORAL DRUG PREPARATIONS

[75] Inventor: Arne Martinus Pedersen, Vanlose, Denmark

[73] Assignee: A/S Alfred Benzon, Copenhagen, Denmark

[22] Filed: Aug. 27, 1975

[21] Appl. No.: 608,230

Related U.S. Application Data

[63] Continuation-in-part of Ser. No. 453,032, March 20, 1974.

[52] U.S. Cl. .................................. 424/21; 424/19; 424/20; 424/22; 424/31; 424/32; 424/81
[51] Int. Cl.$^2$ ...................... A61K 9/22; A61K 9/32
[58] Field of Search ............................... 424/19–22, 424/32, 33, 81

[56] References Cited
UNITED STATES PATENTS

| | | | |
|---|---|---|---|
| 2,971,889 | 2/1961 | Swintosky | 424/31 |
| 3,247,066 | 4/1966 | Milosovich | 424/21 X |
| 3,538,214 | 11/1970 | Polli et al. | 424/19 |
| 3,577,512 | 5/1971 | Shepherd et al. | 424/21 |
| 3,608,063 | 9/1971 | Banker | 424/22 |
| 3,629,393 | 12/1971 | Nakamoto et al. | 424/22 |
| 3,641,237 | 9/1972 | Gould et al. | 424/16 |
| 3,689,634 | 9/1972 | Kliment et al. | 424/21 |
| 3,775,537 | 11/1973 | Lehmann et al. | 424/21 |

OTHER PUBLICATIONS

Lehmann, K. Pharm. Ind. 29(6): 396–398 (1967) Acrylic Resin Lacquers for Preparation of Depot Medicinal Forms.
Lehmann, K. et al. Pharm. Ind. 31(5): 319–322 (1969) Permeable Acrylic Resin Lacquers for Production of Medicinal Depot Forms II. (1).
Lehmann, K. et al. Pharm. Ind. 31(6): 409–412 (1969) Permeable Acrylic Resin Lacquers for Production of Medicinal Depot Forms II. (2).
Lehmann, K. et al. Drugs Made Ger. 16(4): 126, 131–132, 134, 136 (1973) Use of Aqueous Synthetic–Polymer Dispersions for Coating Pharmaceutical Dosage Forms.
Lehmann, K. et al. Labo–Pharma–Probl. Tech. 22 (228): 57–62, 65 (1974) Use of Aqueous Plastic Dispersions for Coating Pharmaceutical Forms.
Lehmann, K. Mfg. Chem. Aerosol News. 45(5): 48, 50 (1974) Polymer Coating of tablets. Versatile Technique.

*Primary Examiner*—Shep K. Rose
*Attorney, Agent, or Firm*—Merriam, Marshall, Shapiro & Klose

[57] ABSTRACT

Oral drug preparations are described, having a protracted effect and a suitable rate of release of the drug during its period of action, said preparations comprising a pharmaceutically active component to which has been admixed one or more buffers, and possibly other pharmaceutically acceptable adjuvants, the mixture having been shaped into small particles and subsequently been coated with a film-forming material allowing for diffusion of stomach juice and intestinal juice together with the drugs dissolved therein, but not being soluble in the said juices.

1 Claim, No Drawings

ORAL DRUG PREPARATIONS

This application is a continuation-in-part of my application Ser. No. 453,032, filed Mar. 20, 1974.

The present invention relates to new oral drug preparations having a protracted effect and a suitable rate of release of the active component during the period of action.

The oral drug preparations of the invention comprise an active component, possibly admixed with pharmaceutically acceptable adjuvants, which has been shaped into small spheroidal particles, and subsequently coated with a film-forming material allowing for diffusion of stomach juice and intestinal juice together with drugs dissolved therein, but not being dissolved by the said juices.

While passing through the human digestive tract, orally administered drugs are subjected to pH-values varying from 1.0 to 7.4. Thus the saliva of the mouth has a pH of 7, the stomach juice of a fasting person has normally a pH of 1, which may vary between 1.0 and 4.0 pursuant to consumption of food, bile has pH 7.0 to 7.4, and in the intestines pH is 5 to 7.

Moreover, the orally taken drug stays for varying periods in the individual parts of the digestive tract.

Together with the fact that the solubility of many drugs is dependent upon the pH of the solvent medium this results in making it extremely difficult to obtain even approximately the same rate of release everywhere in the digestive tract, even if attempts in this respect have not been missing.

Thus, it has been proposed to use combinations of coatings which are soluble in the stomach juice and the intestinal juices, respectively. By producing a tablet, for example, by first coating a smaller tablet of the active substance with a layer of a material not soluble in the stomach juice, but soluble in the intestine juices, and then depositing a layer of the active substance upon this coating, which is again coated with a layer of a material soluble in the stomach juice, part of the active substance will be released in the stomach, the remainder being released in the intestines. Thus, the period of action can be prolonged, but the release takes place in portions and owing to the pH dependent solubility of the coatings, the released drug will be available for different periods from time to time.

Better results have been achieved by using coatings of various synthetic polymers which have been modified by means of solubilizing groups, e.g. quaternary ammonium groups. Thus, it is possible to produce coatings, the solubility and the permeability of which are independent of the physiological pH within the range 2-8, since by carefully adjusting the content of quaternary ammonium groups to a low value, it is possible to obtain coatings being insoluble, but to some extent swelling in water. In principle, such coatings function in the way that stomach juice or intestinal juice diffuses in or out through the coating, gradually dissolving the active substance.

More recently, the efforts have been directed to finding suitable combinations of polymers in order to control the diffusion rate and thereby the release of the coated active substance, cf. the U.S. Pat. No. 3,775,537.

Even if it is maintained that a pH independent release of the enclosed drugs can be obtained by means of these coatings, experiments have shown, however, that this is not always so and that often individual adjustment of the properties of the coating is necessary, when the active substance is replaced by another active substance.

It is an object of the present invention to provide drug preparations of the said kind in the form of small spheroidal particles having a coating thereon of a film-forming acrylic polymer drug-diffusing dragee lacquer, which without any individual adjustment of the coating ensures a pH independent release of the active substance at a substantially constant rate.

This is accomplished, according to the invention, by the addition to the material, from which the particles are prepared, of a buffer or mixture of buffers which is so chosen, dependent upon the kind of active substance, that a suitable pH is obtained for dissolving said active substance in the body fluid permeating the coating.

By thus ensuring release of the active substance at constant pH irrespective of the ambient pH, there is no need for adjustment of the properties of the coating after the kind of active substance in the preparation, so that the same composition of the coating used for any kind of active substance will give a substantially constant rate of release. Changes in the thickness of the applied coating, or in the composition of the coating thus only serves to control the amount of released active substance per unit of time.

Thus, any of the commercially available acrylic polymer film-forming dragee lacquers may be used for the coating of the present drug preparations, but at present the dragee lacquers marketed by Rohm Pharma GmbH, Darmstadt, German Federal Republic, under the registered trade name EUDRAGIT, and of compositions as described in the U.S. Pat. No. 3,775,537, are preferred, possibly with admixed plasticizer.

The buffer or mixture of buffers is chosen, having regard to the stability and solubility also of the other components of the preparation, so as to impart a pH-value from 1 to 7.5, preferably from 4 to 6, to the buffered system.

The buffers to be used should be physiologically acceptable and could be e.g. primary, secondary, or tertiary salts of phosphoric acid, or salts of phthalic acid, citric acid, tartaric acid, or salts of amino acids, e.g. glycine, or mixtures of the said buffer salts.

The amount of buffer must be sufficient to ensure a buffer effect during the time it takes for the drug to be released from the composition particles. Thus, the proportion of buffer to drug will be dependent on the rate of diffusion of both through the coating material, and is easily determined by simple tests for a given combination of drug, buffer and coating material.

The diameter of the spheroidal particles will generally be from 0.1 to 5 mm, preferably 0.5 to 1.5 mm.

The mode of action of the compositions obtained in this manner is as follows:

The fluids in the digestive tract, e.g. stomach juice and intestine juice, can penetrate through the coating, acting as a diffusion membrane. The fluid thus passing through the coating into the interior of the particles will dissolve the buffer and thus get a pH suitable for dissolving and possibly ionizing the drug to create a solution of it in equilibrium with solid matter. Owing to the differences in concentration on the inner and outer sides of the membrane, the said solution will diffuse out into the surrounding body fluid, and further fluid will pass in so that a slow, substantially constant release of the drug takes place, and this will be independent of the pH of the body fluid proper.

An additional advantage is as hereinbefore mentioned that an adjustment of the coating composition to the kind of drug used becomes unnecessary, since instead the drug is adjusted by means of the buffer which is by far easier than an adjustment of the composition of the coating to the individual drugs.

The drugs, which may be used in the preparations of the invention, may be of acid as well as of basic or neutral character in solution. As examples of the former may be mentioned valeric acid, ascorbic acid, 1-(m-trifluoromethylphenyl)-2-(N-ethylamino)-propane, HCl, and barbituric acids, whereas ephedrine, atropine, pyridoxine, and codeine are examples of drugs of basic character, and reserpine and theophylline are examples of drugs forming neutral solutions.

The following experiment is illustrative of the effect obtained by the preparations of the invention.

In the experiment a coating composition consisting of the following ingredients was used:

|  | Parts by Weight |
|---|---|
| Acrylic polymer (12.5% solution in isopropanol-acetone (3:2)) | 50 |
| Pigment | 0.667 |
| Talc | 9.833 |
| Acetyltributyl citrate | 0.74 |
| Isopropanol ad | 100 |

With this composition, two lots of cores A and B withouth and with buffer, respectively, were coated, the compositions of A and B in parts by weight being as follows:

| | | |
|---|---|---|
| 1-(m-Trifluoromethylphenyl)-2-(N-ethylamino)-propane,HCl | 40.0 | 40.0 |
| Saccharose | 38.0 | 17.0 |
| Microcrystalline cellulose | 20.0 | 20.0 |
| Hydroxypropyl cellulose | 2.0 | 3.0 |
| Monosodium phosphate | — | 20.0 |

The release of the drug in synthetic stomach juice and intestinal juice having a pH of 1.5 to 7.2, respectively, was determined periodically. The results are given in the following table, the figures representing the weight percent of the total content of the drug, which was released within the stated period.

| Composition | pH | Percent by weight released after hours | | | | | | | |
|---|---|---|---|---|---|---|---|---|---|
| | | 1 | 2 | 3 | 4 | 5 | 6 | 7 | 8 |
| A | 1.5 | 10 | 17 | 20 | 36 | 42 | 88 | 92 | — |
| B | 1.5 | 3.5 | 7 | — | 13.5 | — | 24.5 | — | 45.5 |
| A | 7.2 | 3.5 | 8 | 15 | 22 | 40 | 77 | 87 | — |
| B | 7.2 | 4 | 6.5 | — | 11 | — | 22 | — | 45 |

The table shows that the release of the drug of composition B is proportional to the time and independent of the pH.

I claim:

1. An oral drug preparation having a protracted effect and a substantially constant rate of release of the drug, comprising an admixture, of a drug and an effective amount of a buffer acid, buffer acid salts, and mixtures thereof, in the form of small spheroidal particles of 0.1 to 5 mm diameter, said particles having a coating thereon of a film-forming acrylic polymer drug-diffusing dragee lacquer, allowing for diffusion of the stomach and intestinal juices through the coating, but not being soluble in said juices.

* * * * *